United States Patent [19]

Buechel et al.

[11] Patent Number: 4,623,353

[45] Date of Patent: Nov. 18, 1986

[54] STEM-TYPE FEMORAL PROSTHESIS INCLUDING A COLLAR PROVIDED WITH ACCESS SLOTS FOR BONE RESECTIONING MEANS

[76] Inventors: Frederick F. Buechel, 76 Crest Dr., South Orange, N.J. 07079; Michael J. Pappas, 61 Gould Pl., Caldwell, N.J. 07006

[21] Appl. No.: 830,207

[22] Filed: Feb. 18, 1986

Related U.S. Application Data

[62] Division of Ser. No. 574,037, Jan. 26, 1984.

[51] Int. Cl.⁴ ............................................. A61F 2/32
[52] U.S. Cl. ..................................................... 623/23
[58] Field of Search ....................... 623/20, 16, 21, 17, 623/22, 18, 23, 19; 128/92 B, 92 C, 92 CA

[56] References Cited

U.S. PATENT DOCUMENTS 2,765,787  10/1956  Pellet ............................ 128/92 CA

FOREIGN PATENT DOCUMENTS 0012146  6/1980  European Pat. Off. .............. 623/22
2754352  5/1979  Fed. Rep. of Germany ........ 623/22
0492277  11/1975  U.S.S.R. .............................. 623/23

Primary Examiner—Richard J. Apley
Assistant Examiner—David J. Isabella
Attorney, Agent, or Firm—R. Gale Rhodes, Jr.

[57] ABSTRACT

Stem-type femoral prostheses including a collar disposed transversely on the proximal end of the stem and including portions extending outwardly anteriorly and posteriorly of said stem, the prosthesis for implantation in the proximal end of a femur, the collar is provided with a pair of access slots extending a predetermined distance inwardly into the collar portions extending outwardly anteriorly and posteriorly of said stem; the access slots extend generally in the lateral to medial direction, and upon implantation of the prosthesis in the femur, the prosthesis and femur develop prosthesis-bone fixation interfaces and the slots provide access to bone resection means to facilitate resectioning of the prosthesis-bone fixation interfaces thereby facilitating removal of the implanted prosthesis from the femur.

2 Claims, 2 Drawing Figures

४,६२३,३५३

STEM-TYPE FEMORAL PROSTHESIS INCLUDING A COLLAR PROVIDED WITH ACCESS SLOTS FOR BONE RESECTIONING MEANS

CROSS-REFERENCE TO RELATED APPLICATION

This application is a divisional application of U.S. patent application Serial No. 574,037, filed Jan. 26, 1984, entitled IMPROVED FEMORAL STEM-TYPE PROSTHESIS, Michael J. Pappas and Frederick F. Buechel inventors.

BACKGROUND OF THE INVENTION

A femoral stem-type prosthesis employing a collar as shown in U.S. Pat. No. 4,404,693 patented Sept. 20, 1983, Karl Zweymüller inventor; U.S. Pat. No. 4,406,023 patented Sept. 27, 1983, William H. Harris inventor; and German Patent No. 26 45 100 patented Apr. 6, 1978, Fritz Hofmeister et al. inventors, are more difficult to remove in the event of post-operative complications than essentially collarless type prostheses such as those described in U.S. Pat. No. 4,310,931 patented Jan. 19, 1982, Maurice E. Müller inventor, since collars reduce access to the fixation surfaces of the femoral stem.

In a collarless type prosthesis such as described by Müller, in the event of need for removal, a thin surgical cutting instrument such as an osteotome or saw blade can be passed superiorly between the fixation surface of the prosthesis and the cortical shell of the proximal femur. This cutting instrument can then be moved inferiorly cutting away the interface between the prosthesis, or in the event cement is used, between the cement and bone or cement and prosthesis, so as to loosen the stem without disturbing significantly the load supporting cortical shell of the femur. Thus, the load supporting cortical shell can essentially be left intact making possible implantation of another stem without difficulty and with the expectation of good results. On the other hand, where a calcar collar is employed the collar generally extends outwardly from the neck and stem of the prosthesis covering the cortical shell of the femur generally anteriorly, medially and posteriorly. With such a collar, it is no longer possible to pass a cutting instrument between the stem of the prosthesis and the cortical shell. As a result, removal of an implanted firmly fixed femoral stem is made more difficult. Generally in cemented prosthesis since the interfacial strength between the prosthesis and cement is relatively weak, the stem can be removed by impacting the stem so as to withdraw it from the femoral cavity. Once the stem is removed, the cement mantle is accessible for removal. Where the stem, however, is fixtured by biological means such as the stem shown in Hofmeister et al. where bone is intended to grow into apertures in the stem, and the porous coated femoral stems now in common use such as the AML ® stem sold by DePuy, a Division of Boehringer Mannheim Corporation, removal of a firmly fixtured femoral stem is often accompanied by substantial loss of the bone of the proximal femur since under such circumstances such impaction will often produce fracture of the cortical shell of the proximal femur and attendant bone loss. Under such circumstances, revision using another stem becomes much more risky and is often attendant by leg length shortening because of this bone loss.

One approach to dealing with this problem is described in U.S. Pat. No. 4,514,865 patented May 7, 1985, William H. Harris inventor, wherein Harris employs a collar contacting cortical bone essentially only along the medial border of the calcar. With such a collar and particularly if there is no porous surface for bone ingrowth on the lateral portion of the femoral stem, removal can be accomplished as described earlier for collarless type prostheses. The disadvantage of this design, however, is that it compromises performance for the overwhelming majority of cases where removal is not necessary in order to provide more convenient removal in a few instances. The load bearing surfaces of the calcar of the most proximal portion of the cortical femoral shell exposed after resection of the neck carries load not only along its lateral border but also its anterior and posterior edges; thus, the somewhat abbreviated collar used by Harris provides less load transfer capability than conventional collar configurations.

SUMMARY OF THE INVENTION

The object of this invention is to provide a load bearing collar of a stem-type femoral prosthesis similar in load bearing capabilities to conventional collars but having the accessibility of the collar disclosed in the above-noted patent to Harris.

Improved stem-type femoral prosthesis embodying the present invention overcoming the above-noted prior art problem includes a collar disposed transversely on the proximal end of the femoral stem and which collar includes portions extending outwardly anteriorly and posteriorly of the stem which are provided with a pair of access slots extending inwardly into such collar portions and which access slots provide access to bone resection means to facilitate resectioning of prosthesis-bone fixation interfaces thereby facilitating removal of the implanted prosthesis.

DESCRIPTION OF THE DRAWINGS

Figure 1:
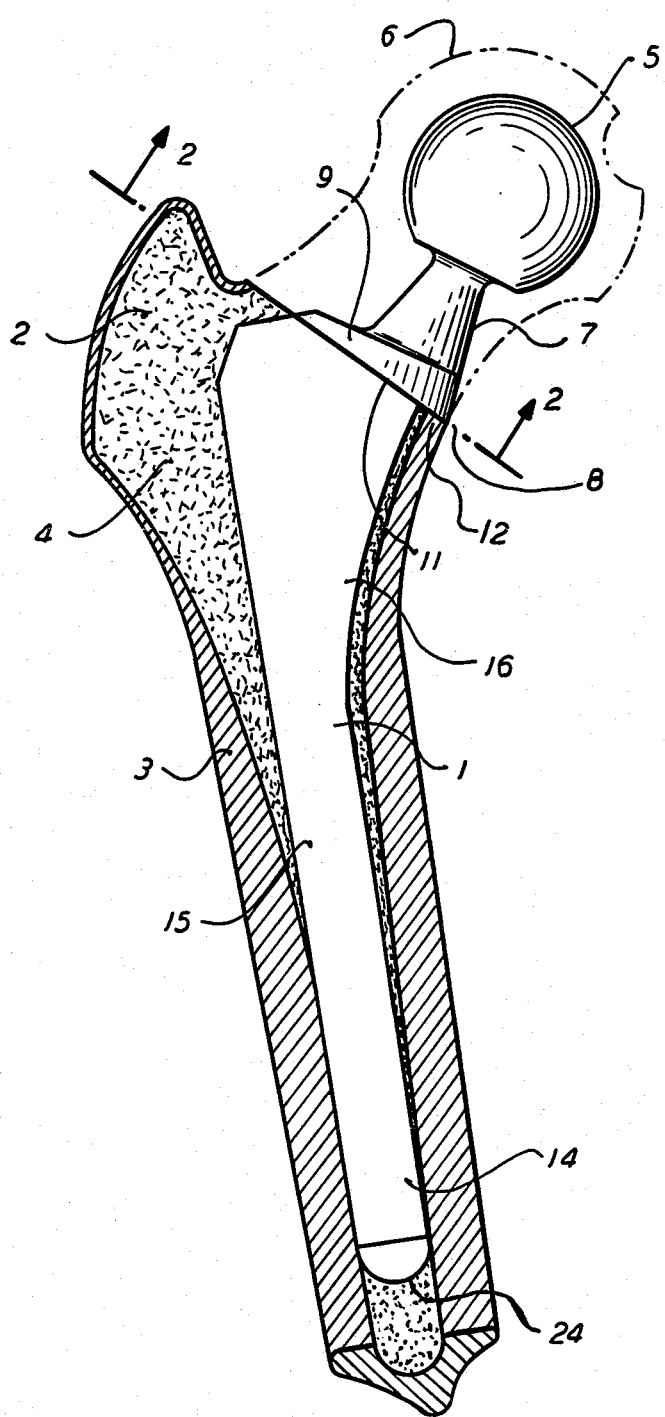
FIG. 1 shows a stem-type femoral prosthesis including a collar embodying the present invention and implanted in a femur shown in cross-section with the natural femoral head shown in phantom.

FIG. 1 shows a stem-type femoral prosthesis 1 embodying the present invention and implanted in the proximal end of a femur 2; the prosthesis 1 includes a head 5, neck 7, collar 9 having an inferior surface 11, stem 15 having a proximal end or portion 16 and a distal end 14. The collar 9 is disposed transversely of the proximal end 16 of the stem 15 and, as may be better seen in FIG. 2, includes collar portions 21 and 22 extending outwardly anteriorly and posteriorly of the stem 15, particularly the proximal portion 16 of the stem. The femur consists of an outer shell of cortical bone 3 and inner cancellous bone 4. The head 5 of the femoral component is highly polished and articulates with a natural acetabulum or an acetabular prosthesis. The medial exterior shape 10 of collar 9, FIG. 2, closely matches the cross-section of the resected neck of the femur 2 so that the inferior surface 11 of the collar contacts the cortical bone 12 of the resected femur; the resected and prepared proximal end of the femur 2 is shown in FIG. 1. Upon (at and/or after) implantation of the stem-type femoral prosthesis 1 in the femur 2 as shown in FIG. 1, such as by the use of cement 24 or by direct bone ingrowth fixation upon the prosthesis stem being porous coated as disclosed in the above-referenced U.S. Pat. No. 4,406,023 to Harris, prosthesis-bone fixation interfaces will develop, particularly between the stem 15 and femur 2, and for removal of the implanted prosthesis 1 from the femur 2, such prosthesis-bone fixation interfaces, inter alia, must be destroyed or resected.

Figure 2:
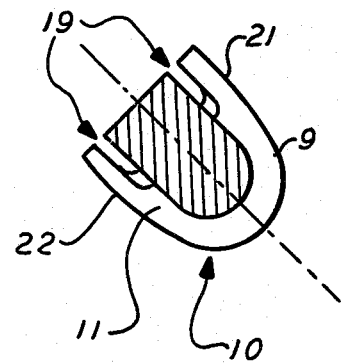
FIG. 2 is a cross-sectional view taken along the line 2—2 in FIG. 1 and in the direction of the arrows.

Destruction or resection of such prosthesis-bone fixation interfaces for prosthesis removal is greatly enhanced by the provision of the access slots 19, FIG. 2, which permits bone resection means, such as an osteotome or thin bone cutting instrument, to be inserted downwardly into the access slots 19 to accomplish resection or destruction of the above-noted prosthesis-bone fixation interfaces thereby greatly facilitating removal of the implanted prosthesis 1 from the femur 2.

It will be understood that many variations and modifications may be made in the present invention without departing from the spirit and the scope thereof.

What is claimed is:

1. In stem-type femoral prostheses for implantation in the resected proximal end of a femur and including a collar disposed transversely on the proximal end of the stem for engaging and covering at least a portion of said resected proximal end of said femur, said collar including portions extending outwardly anteriorly and posteriorly of said stem, wherein the improvement comprises:

said collar portions extending outwardly anteriorly and posteriorly of said stem having a pair of access slots having inner and outer walls extending a predetermined distance inwardly thereinto along said stem generally in the lateral to medial direction and extending entirely therethrough in the superior to inferior direction, and upon implantation of said prosthesis in said femur, said stem and femur developing stem-bone fixation interfaces and said slots providing access to bone resection means to be inserted downwardly through said slots to facilitate resectioning of said stem-bone fixation interfaces continuously along said predetermined distance of said slots thereby facilitating removal of said implanted prosthesis from said femur.

2. Prosthesis according to claim 1 wherein said access slots are contiguous to said stem to facilitate resectioning of said stem-bone interfaces by said resectioning means in a direction generally parallel to said stem.

* * * * *